United States Patent [19]

Barberet et al.

[11] Patent Number: Plant 6,288

[45] Date of Patent: Sep. 13, 1988

[54] CARNATION NAMED 'LONCAMPI'

[75] Inventors: Nicole Barberet; Yves Ducloux, both of Antibes, France

[73] Assignee: Laboratoire de Physiologie Vegetale de la Londe, La Londe, France

[21] Appl. No.: 907,859

[22] Filed: Sep. 15, 1986

[51] Int. Cl.[4] ..... A01H 5/00

[52] U.S. Cl. ..... Plt./70

[58] Field of Search ..... Plt./70

*Primary Examiner*—Robert E. Bagwill

*Attorney, Agent, or Firm*—Charles W. Rummler

[57] ABSTRACT

A new variety of spray carnation having a recurrent blooming habit and a profuse production of small, clear white blooms during the spring, midseason and fall intervals, the blooms appearing in clusters at the upper portion of a strong, erect stem and the plant itself being distinguished by its relatively tall growth and its vigorous, upright and rather rigid growth habit with abundant foliage.

1 Drawing Sheet

BACKGROUND OF THE NEW PLANT

This new carnation variety originated as a seedling resulting from our crossing of selected plants from our collection of carnations maintained for breeding purposes at La Londe, Les Maures, France. Our object in making this crossing was to develop a spray carnation having blooms of nice color on a plant having good quality of flower, spray, stem and growth habit, as well as resistance to *Fusarium oxysporum.* This selected plant was reproduced by cuttings at La Londe with such pleasing results that propagation was continued at La Londe by both cuttings and in vitro through several successive generations, which clearly demonstrated that the novel and advantageous characteristics of this new variety appeared to be firmly fixed and would hold true from generation to generation.

DESCRIPTION OF THE DRAWING

This new variety of spray carnation is illustrated by the accompanying photographic drawing which shows, in full color, the upper portion of a typical spray stem bearing buds in various stages of opening and flowers at several stages of maturity, the colors shown being as nearly true to that specified herein as is reasonably possible to obtain by conventional photographic procedures.

DESCRIPTION OF THE NEW PLANT

The following is a detailed description of our new carnation variety based upon observation of greenhouse plants grown at La Londe, Les Maures, France, in the spring of 1986, the color designations being according to the R.H.S. Colour Chart published by The Royal Horticultural Society of London, England.

THE PLANT

Origin: Seedling.

Parentage:

*Seed parent.*—Stock variety 431 MJ.

*Pollen parent.*—Stock variety 76 MB 15. These plant varieties were selected by us from our collection of breeding plants and are individually identified in our permanent records maintained in our office at 83250 La Londe, Les Maures, France.

Classification:

*Botanic.*—*Dianthus caryophyllus* hybrid.

*Commercial.*—Spray carnation.

Form: A tall, erect bush comprising at least four stems emitted from the main stem near the ground.

Height: Averages about 89 cm. at eight months.

Main stem:

*Length.*—Less than 15 cm. due to pinching.

Branching character: Alternate and numerous with twin branches at each branching node in the upper portion of the main stem.

Growth habit: Vigorous, upright and rather rigid.

Foliage:

*Quantity.*—Abundant.

*Number of leaves.*—More than 120.

*Size of leaf at 7th node.*—Averages about 10.9 cm. long and about 0.9 cm. wide.

*Shape.*—Linear with curved margins and acuminate tip.

*Texture.*—Leathery.

*Color.*—Both upper and lower sides, 189A.

*Leaflets.*—None.

*Ribs, veins and rachis.*—Hardly noticeable.

THE BUD

Size: Small.

*Diameter.*—Averages about 1.2 cm.

*Length.*—Averages about 2.4 cm.

Shape: Long ovoid.

Rate of opening: Normal for carnations.

Color of petals:

*When sepals first divide and when petals begin to unfurl.*—White 155B.

Sepals:

*Number.*—5 to 7.

*Shape.*—joined together at the lower part with the upper part somewhat oval in shape and having an acuminate apex. The sepals are hooded over the bud before dividing and stand up as the flower opens.

*Color.*—Inside — 145D. Outside — 145B and 138 B.

*Striae.*—Longitudinal.

Calyx:

*Shape.*—Long cylindrical.

*Aspect.*—Smooth.

*Splitting.*—The calyx does not split.

Flowering stem:

*Length.*—About 55.8 cm., in average.
*Character.*—Erect.
*Color.*—189A.

THE FLOWER

Blooming habit: Recurrent and profusely during spring, midseason and fall blooming periods with a tendency to give fewer blooms in the fall.
Borne: In a cluster.
Size of bloom: Small.
*Diameter.*—Averaging about 5 cm.
*Depth.*—Averaging about 4.6 cm.
Shape:
*When bloom first opens.*—High-centered.
*When bloom matures.*—Dome-shaped.
Petalage:
*Number of petals.*—About 36, in average.
*Arrangement.*—Imbricated.
*Form.*—Fan-shaped with rounded edges and very lightly serrated at the apex margin.
*Texture.*—Leathery.
*Aspect.*—Shiny.
*Color.*—The upper and reverse sides of both outer and inner petals, 155B. Base of outer petals, greenish.
Petaloids:
*Number.*—Less than six.
*Size.*—Smaller than petals.
*Color.*—155B.
Flower stem, cut at 10th node:
*Length.*—About 55.8 cm., in average.
*Character.*—Upright with good strength.
*Color.*—189A.

Fragrance: Perceptible.
Persistence: The flowers hang on and dry.
Lasting quality:
*As cut flower.*—At least ten days in vase keeping.

REPRODUCTIVE ORGANS

Stamens:
*Number.*—3 to 6.
*Arrangement.*—Around the ovary.
*Anthers.*—Size: About 4 mm. Color: White.
*Filaments.*—Length: About 10 mm., in average. Color: Whitish.
Pistils:
*Number.*—2 or 3.
*Styles.*—Length: About 11 mm., in average. Color: White.
*Stigma.*—Color: White.
Character of ovary: Ribbed.

This spray carnation variety most nearly resembles the variety 'Lonblitec' (U.S. Plant Pat. No. 5,434) but differs from that variety by having much finer serration of the flower petals, more abundant blooms and a more rigid stem.

We claim:

1. The new and distinctive spray carnation variety, substantially as herein shown and described, characterized by its recurrent flowering habit with profuse production of flowers having a clear white color, and having a rapid, vigorous and upright growth habit with abundant foliage.

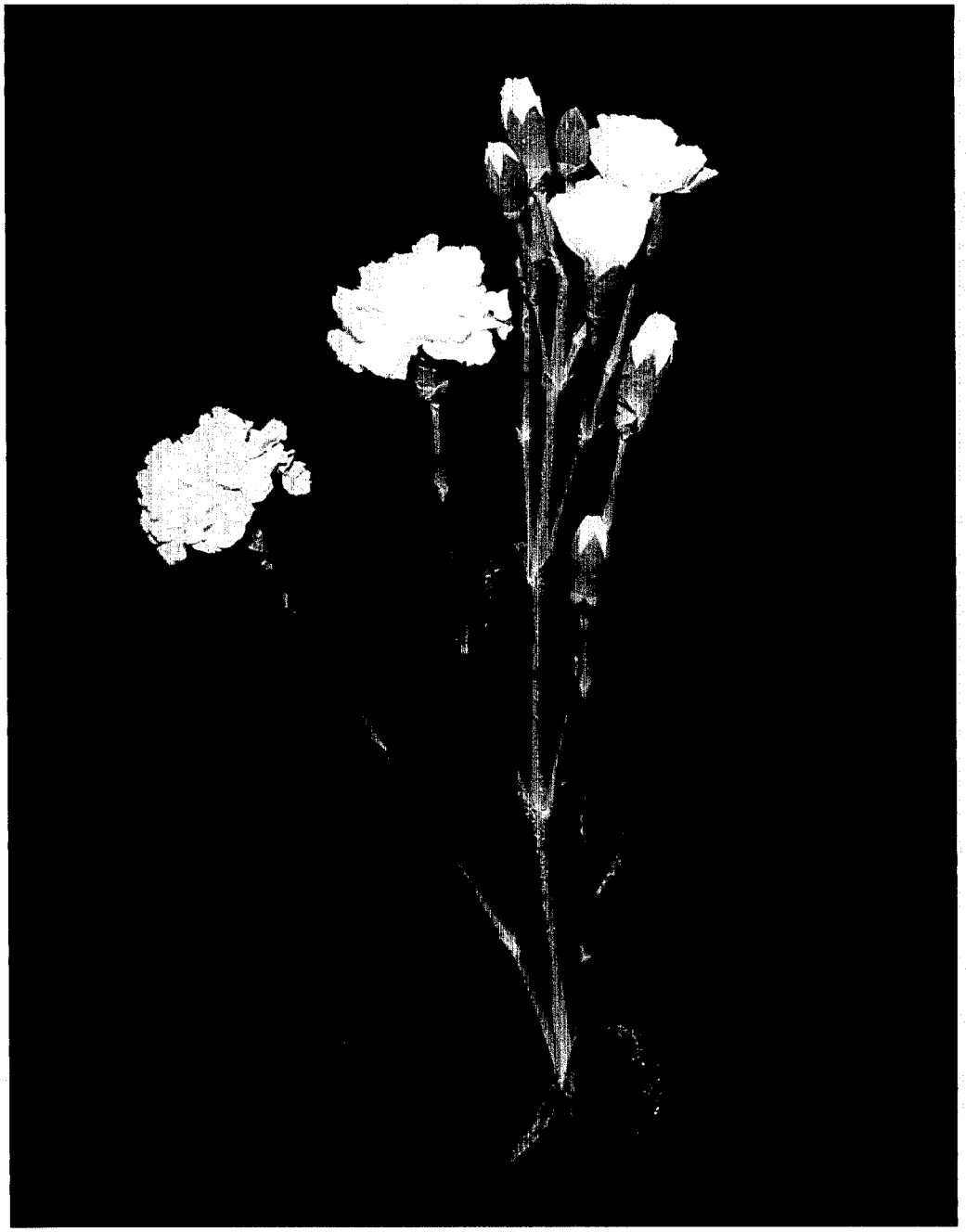

* * * * *